April 11, 1972 J. M. GARABEDIAN Plant Pat. 3,106
GRAPEVINE
Filed April 29, 1970
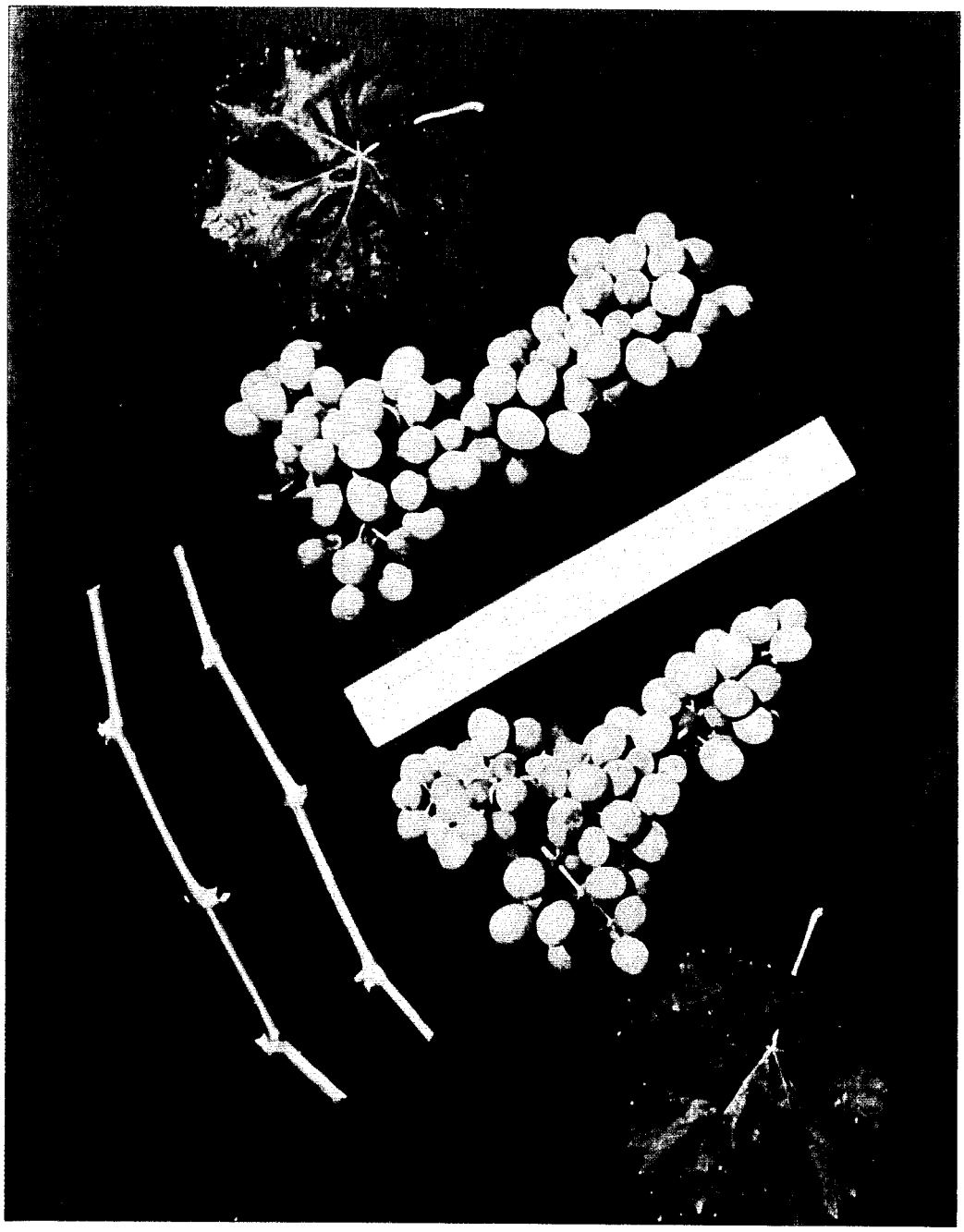
INVENTOR
John M. Garabedian
BY
Webster & Webster
ATTORNEYS

United States Patent Office

Plant Pat. 3,106

Patented Apr. 11, 1972

3,106

GRAPEVINE

John M. Garabedian, 3158 Hamilton St., Fresno, Calif. 93712

Filed Apr. 29, 1970, Ser. No. 33,111

Int. Cl. A01h *5/03*

U.S. Cl. Plt.—47 1 Claim

ABSTRACT OF THE DISCLOSURE

A large, vigorous, productive grapevine having canes of medium length and thickness, long tendrils of medium thickness, dense foliage, medium size leaves with a 2-series margin, medium size fertile flowers, and fruit of which the clusters are of medium to large size, and the berries white, of large size, firm and crisp of flesh, oval to obovoid in form, seedless, and of superior eating quality; the fruit—which does not shatter even when mature—ripening about a week to ten days earlier than the Thompson Seedless (unpatented), and the berries being of relatively larger size and sweeter, with a bitey taste account high acid, and a slightly muscat flavor.

ORIGIN OF THE VARIETY

The present variety of grapevine was originated by me, on a ranch of which I am an owner, located near Madera, Madera County, Calif., as a cross between the Cardinal and an unnamed seedless sport (unpatented) previously found by me in a vineyard (of which I am also an owner) located near Fresno, Fresno County, Calif. The seedling vine, which resulted from the above described cross, was maintained by me under careful and continuing observation, and—upon the vine bearing fruit—I recognized its new and distinctive characteristics and which classed it as a superior table grape. The variety was, therefore, selected for asexual reproduction preparatory to ultimate vineyard planting thereof.

ASEXUAL REPRODUCTION OF THE VARIETY

Subsequent to origination of the present variety of grapevine, and recognition of its advantageous characteristics, I asexually reproduced such variety by budding onto mature Thompson Seedless grapevines in a vineyard on the aforesaid ranch located near Madera, Madera County, Calif. When grown to maturity, and in bearing, such asexual reproductions ran true to the orginal grapevine in all respects.

SUMMARY OF THE VARIETY

The herein claimed new and distinct variety of grapevine is characterized by a large, vigorous, productive vine having canes of medium length and thickness, long tendrils of medium thickness, dense foliage, medium size leaves with a 2-series margin, medium size fertile flowers, and fruit of which the clusters are of medium to large size, and the berries white, of large size, firm and crisp of flesh, oval to obovoid in form, seedless, and of superior eating quality; the fruit—which does not shatter even when mature—ripening about a week to ten days earlier than the Thompson Seedless, and the berries being of relatively larger size and sweeter, with a bitey taste account high acid, and a slightly muscat flavor.

BRIEF DESCRIPTION OF THE DRAWING

The drawing is an illustration, by photographic reproduction in color, of leaves, lengths of cane, and clusters of berries of the variety.

DESCRIPTION OF THE VARIETY

The botanical details of this new and distinct variety of grapevine—with color definitions (except those in common color terms) referenced to Maerz and Paul Dictionary of Color—are as follows:

Vine:

*Size.*—Large.

*Vigor.*—Vigorous.

*Production.*—Productive.

*Trunk.*—Bark—Long straps; much fissured. Color—Dark gray, reddish brown underneath.

*Canes.* — Length — Medium—10′–15′. Thickness—medium; width at node—½″; width at internode—⅝″.

*Nodes.*—Length—Medium. Average distance between nodes 4″–5″.

*Tendrils.*—Length—Long; average length—7″–10″. Thickness — Medium; average thickness — 3/32″. Location—Discontinuous. Leafing—Some produce leaves.

*Color (Matured Cane).*—Raw Sienna brown (13–L–10).

Foliage:

*Density.*—Heavy.

*Leaves (from 9th to 12th node).* — Blade — 3–5 lobed. Size—Medium; length—4½″–7″; width—6″–9″. Form—Petiole sinus—V-shaped, overlapping. Inferior sinus—V-shaped, very shallow. Superior sinus—V-shaped, shallow to medium. Older leaves—Have a bulginess at or near the petiolar sinus similar to Carignane (unpatented). Color—Dorsal side—Dark green, ventral side—Greenish yellow. Margin—2 series, medium, blunt. Smoothness—Glabrous. Petiole—Length—4″–7″. Thickness—3–5 mm. Color—On newer leaves petiole is reddish. On mature leaves: Dorsal Side—Medium green with light pink striations; Ventral Side—Reddish—with green striations.

Flowers:

*Size.*—Medium.

*Location (Node where fruit is produced) mostly 3rd.*—5th node.

*Type.*—Fertile.

*Bloom.*—Date of first bloom—May 3, 1969. Date of full bloom—May 10th—May 12th, 1969. Date of last bloom—May 18, 1969.

*Pedical.*—Color—Green. Smoothness — Smooth. Smoothness—Smooth.
Length—Medium—6–10 mm.

*Pistil.*—Color—Green.

*Stamens.*—Number — 6. Length — Medium. Filaments—Striaght. Length—1.6 mm. Amount of pollen—Abundant.

Fruit:

*Peduncle.*—Length — 1″–1¼″. Width — ⅜″–⅝″. Color—Green. Lignification—Some at point of cane attachment.

*Cluster.*—Form—Conical. Size—Medium to large. Number of clusters per cane—1–3. Average cluster weight—748 g.

*Berry.*—Size—Large. Uniformity of berry size—Variable. Dimensions—Longitudinal axis—¾″–1⅓″; diameter axis—½″–1″. Berry set—Good. Fruiting habit—Productive. Number of berries per cluster—Average—148. Form—Oval to slightly obovoid. Thickness of skin—Thick. Texture of skin—Tough. Color—Greenish yellow. Pulp—Adheres to skin. Berry texture—Firm, Crisp. Juice—Color—Colorless. Solids-sugar (Refractometer Test) Average 15.57° B—July 23, 1969.

Acid—1.24° B. Sugar-acid ratio—12.66° B. Flavor—Muscat. Taste—Bitey (incident to high acid). Capstem — Length — ¼"–½". Color — Greenish. Adherence—Very good. Brush—Short. In most cases brush pulls out of berry with the pedicel. Sometimes rudimentary seeds adhere to the brush upon removal from berry. Torus—With warts. Seeds—Number—None.

*Period of ripening.*—July 15, 1968, July 25, 1969, about a week to ten days earlier than Thompson Seedless.

Storage and shipping quality: Good account high acid.
Eating quality: Excellent.

The present variety resulted from the same cross as the variety of grapevine disclosed in copending plant patent application Ser. No. 33,110.

The grapevine and its fruit herein described may vary in slight detail due to climatic and soil conditions under which the variety may be grown; the present description being of the variety as grown in the Central Valley of Calif.

I claim:

1. A new and distinct variety of grapevine, substantially as illustrated and described, which is characterized by a large, vigorous, productive vine having canes of medium length and thickness, long tendrils of medium thickness, dense foliage, medium size leaves with a 2-series margin, medium size fertile flowers, and fruit of which the clusters are of medium to large size, and the berries white, of large size, firm and crisp of flesh, oval to obovoid in form, seedless, and of superior eating quality; the fruit—which does not shatter even when mature—ripening about a week to ten days earlier than the Thompson Seedless, and the berries being of relatively larger size and sweeter, with a bitey taste account high acid, and a slightly muscat flavor.

No reference cited.

ROBERT E. BAGWILL, Primary Examiner